United States Patent
Matney et al.

(10) Patent No.: US 6,772,638 B2
(45) Date of Patent: Aug. 10, 2004

(54) UT DETECTION AND SIZING METHOD FOR THIN WALL TUBES

(75) Inventors: Russell M. Matney, Lynchburg, VA (US); Mihai G. Pop, Lynchburg, VA (US); Joseph R. Wyatt, III, Lynchburg, VA (US)

(73) Assignee: Framatome Anp, Inc., Lynchburg, VA (US)

( * ) Notice: Subject to any disclaimer, the term of this patent is extended or adjusted under 35 U.S.C. 154(b) by 0 days.

(21) Appl. No.: 10/015,982

(22) Filed: Oct. 30, 2001

(65) Prior Publication Data

US 2003/0079545 A1 May 1, 2003

(51) Int. Cl.[7] .............................................. G01N 29/10
(52) U.S. Cl. ........................................ 73/627; 73/622
(58) Field of Search ........................ 73/598, 620, 622, 73/600, 623, 627, 629

(56) References Cited

U.S. PATENT DOCUMENTS 4,299,128 A * 11/1981 Gruber ........................ 73/627

* cited by examiner

Primary Examiner—John E. Chapman
(74) Attorney, Agent, or Firm—Vytas R. Matas

(57) ABSTRACT

A method for sizing cracks is disclosed using a combination of depth crack sizing methods to improve crack sizing accuracy for thin walled tubing and tight crack surface openings less than 0.001 inches for cracks of any depth. The tube or plate wall can consist of a single material or multiple metallic electrodeposited or otherwise intimately bonded layers of materials with different magnetic properties and the sizing method comprises known depth sizing methods such as shear wave, time of flight and the selective use of two unique depth sizing methods designated as Mode Converted Signal (MCS) and Full Skip Normalization (FSN) which provide correction factors for the known sizing methods.

9 Claims, 5 Drawing Sheets

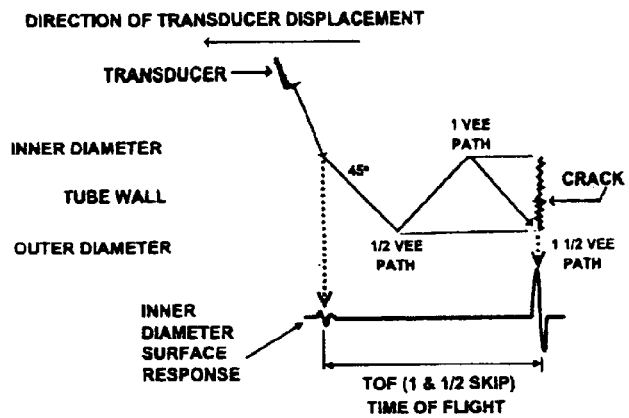

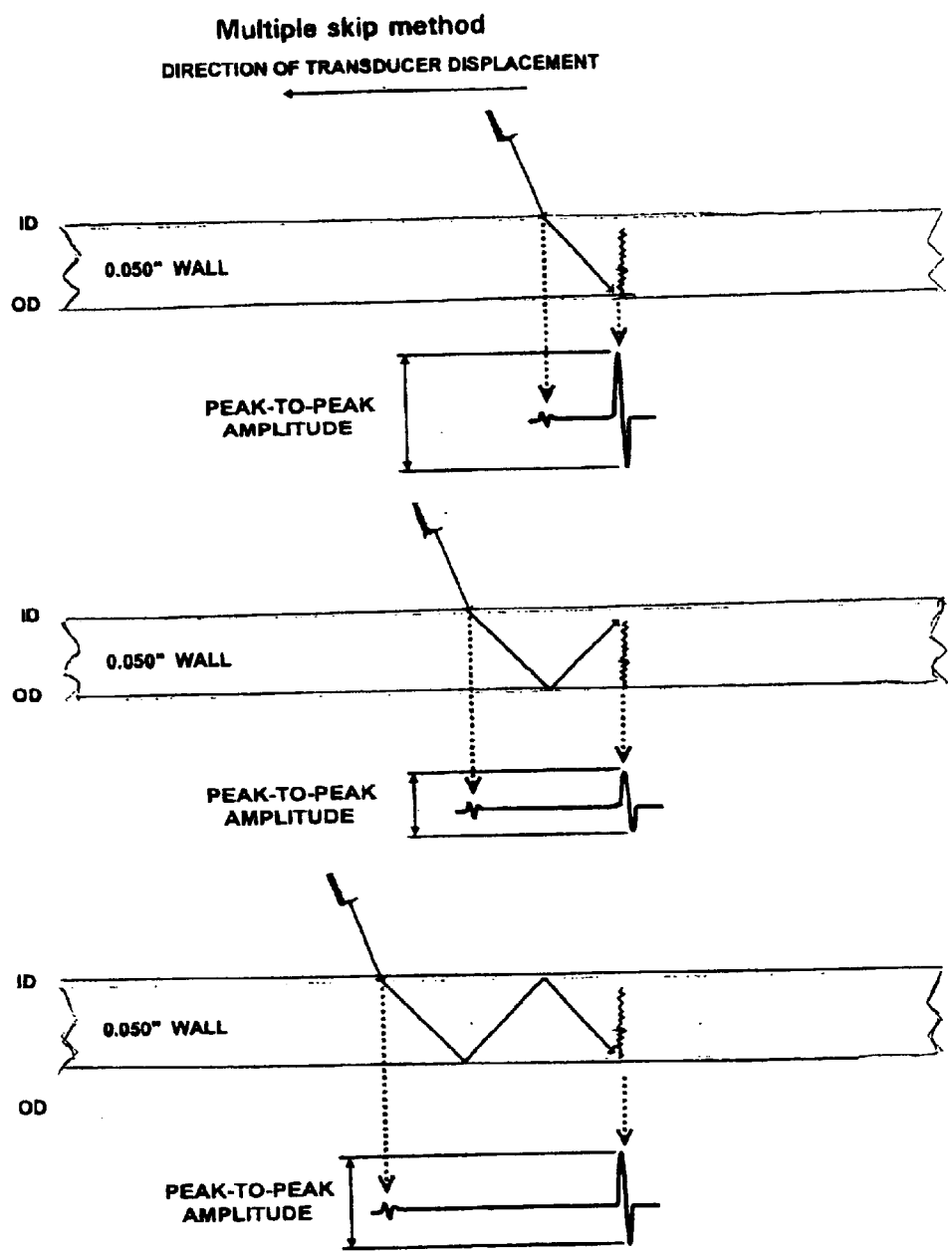

TABLE 1
MODE CONVERTED SIGNAL SIZING RESULTS

| NOTCH DEPTH | UNCORRECTED UT DEPTH ESTIMATE (based on TM TOF) | TM TOF DEPTH ERROR | UNCORRECTED TOF DEPTH PREDICTION | CORRECTED TOF DEPTH PREDICTION (* 1.6 factor) | MCS CORRECTED DEPTH ERROR |
|---|---|---|---|---|---|
| 0.045 | 0.026 | 0.019 | 0.028 | 0.042 | -0.003 |
| 0.040 | 0.024 | 0.016 | 0.025 | 0.038 | -0.002 |
| 0.035 | 0.022 | 0.013 | 0.022 | 0.035 | 0.000 |
| 0.030 | 0.018 | 0.012 | 0.019 | 0.029 | -0.001 |
| 0.025 | 0.016 | 0.009 | 0.016 | 0.026 | 0.001 |
| 0.020 | 0.012 | 0.008 | 0.013 | 0.019 | -0.001 |
| 0.015 | 0.008 | 0.007 | 0.009 | 0.013 | -0.002 |
| 0.010 | 0.005 | 0.005 | 0.006 | 0.008 | -0.002 |

MODE CONVERSION METHOD EXAMPLE

FIG. 6

TABLE 2
COMPARISON OF CONVENTIONAL TOF ANALYSIS TO MCS ANALYSIS

|  | Mode Converted Correction Analysis | Conventional UT TOF Analysis |
|---|---|---|
| Average Error | -0.001 inches | -0.011 inches |
| Error Standard Deviation | 0.001 inches | 0.005 inches |
| Maximum Under-call | -0.003 inches | -0.019 inches |
| RMSE | 0.002 inches | 0.012 inches |
| Lower 95% Confidence Limit | -0.003 inches | -0.019 inches |

FIG. 7

TABLE 3
TYPICAL FULL SKIP NORMALIZATION VALUES

| PROBE: PP5-8 | | FOCAL POINT: ID SURFACE | | |
|---|---|---|---|---|
| REMAINING WALL@ EDM (inch) | 1/2 SKIP (A/D Counts) | 1 SKIP (A/D Counts) | 1 & 1/2 SKIP (A/D Counts) | NORMALIZED RESULT |
| 0.005 | 168 | 135 | 137 | 0.89 |
| 0.010 | 159 | 92 | 96 | 0.72 |
| 0.015 | 144 | 74 | 84 | 0.65 |
| 0.020 | 151 | 46 | 82 | 0.39 |
| 0.025 | 125 | 36 | 99 | 0.32 |
| 0.030 | 113 | 17 | 74 | 0.18 |
| 0.035 | 96 | N/A | 72 | - |
| 0.040 | 82 | N/A | 38 | - |
| 0.045 | 46 | N/A | 44 | - |

TABLE 4
FSN VS REMAINING WALL

| SAMPLE | INDEX | FSN VALUE | Regression Estimate (inch) | Actual Remaining Wall (inch) | Delta (inch) |
|---|---|---|---|---|---|
| 47 | 100 | .89 | 0.003 | 0.000 | -0.003 |
| 47 | 135 | 1.16 | 0.000 | 0.000 | 0.000 |
| 57 | 298 | .32 | 0.021 | 0.028 | 0.007 |
| 57 | 305 | .73 | 0.008 | 0.005 | 0.003 |

UT OD INITIATED CRACK SIZING LOGIC

UT DETECTION AND SIZING METHOD FOR THIN WALL TUBES

BACKGROUND OF THE INVENTION

1. Field of the Invention

The present invention generally relates to methods for sizing the depth of cracks in thin walled tubes or plates and more particularly to improved methods for measuring small cracks in both thin wall tubing and thin wall plates.

2. Description of the Prior Art

The presently known sizing methods for detecting cracks in thin wall tubes are based on transverse (shear-wave) ultrasonic waveform analysis.

The analysis of shear wave data presently uses three basic methods to estimate the depth of such a crack. The three methods are identified as tip diffraction method, the multiple skip method and the target motion time of flight (TOF) method. They are all applicable to pulse echo ultrasonic testing methods.

Cracks in thin walled tubing typically have openings or gaps that are less than 0.001 in. deep and are propagated normal to the crack initiation surface. Ultrasonic testing methods use shear wave techniques to detect and depth size these cracks. These techniques transmit an ultrasonic angle beam pulse (shear wave) which is propagated within the wall in a path that resembles a "V" as best seen in FIG. 1. In this figure, the time of flight (TOF) equals the time difference between the incident inner surface reflection and the corner reflector formed by the outer diameter surface and the crack intersection.

The use of a 45 degree shear wave angle shown in FIG. 1 has been shown to be the optimum angle for the detection of planar flaws in thin wall tubes. Refracted angles less than 45 degrees reduce the reflected energy from planar flaws that propagate normal to the tube wall. Refracted angles greater than 45 degrees provide a longer transmission and attenuation path. Refracted angles less than 45 degrees have reduced reflected signal amplitude and have a reduced ability to separate closely spaced flaws. For example, smaller angles (normal or zero degrees beam) are blind to tight crack like flaws.

The most accurate known depth sizing method is the tip diffraction method. It is based on the detection of a reflection signal from the crack's tip. This method is best understood by referring to FIG. 2 for the following discussion.

The detection of a crack tip signal is indicated therein by a return signal that has a waveform reflection from the crack's tip in addition to a waveform reflection from the crack's corner reflector. This crack tip signal is rarely observed in real cracks for two reasons. First, the reflection from the tip requires a minimum crack width, or gap, of one tenth of a wavelength. The second reason is that a tip reflection signal cannot be distinguished from the corner reflector signal until the crack depth of penetration exceeds one wavelength. The time of flight for these two reflection signals overlap until this depth of penetration is achieved. For a 10 Hz transducer, the depth of penetration equivalent to one wavelength is 0.012 inches, and the minimum gap is equal to 0.0012 inches. For depths of penetration greater than one wavelength, the tip reflection signal should be distinguishable from the corner reflector signal.

Unless both of the above conditions are met, it is unlikely that a crack tip signal can be detected and used for sizing small cracks.

The multiple skip method displayed in FIG. 3 recognizes the presence of the three skip reflections as an indication of a crack's depth of penetration. As the depth of penetration increases, the amplitude of the inner diameter (full) response increases relative to the outer diameter (half and one and one half) skip amplitudes. When a crack produces significant reflection signals at the half skip, full skip, and a one and one half skip positions, the depth is considered to be near through wall. This association of multiple skips and deep depth of penetration has destructive evaluation (DE) support. Based upon the theory that any reflector of depth sufficient to trap a wavelength will produce a significantly large amplitude return, significant return signals should be received when the remaining wall is less than 0.012 inch for a typical 10 MHz transducer.

The Target Motion Time of Flight Method uses the half skip's target motion time of flight information to determine the crack's depth of penetration. In the absence of reflections at the expected full skip, the analyst estimates depth using the earliest or latest detected reflections along the target motion for the outer diameter, half skip signal. This method assumes that the reflections are forty-five degree shear wave returns from the crack face. It also assumes that the earliest and latest detection reflections are coincident with the crack's tip. The crack depth is the difference between the measured depth of the corner reflection and either of the earliest or latest detection. Target motion TOF is the most accurate method for determining the location of a corner trap. However, the method may not accurately locate the crack tip, resulting in the failure to accurately depth size the crack.

Given an acceptable 45 degree shear wave calibration, where the depth associated with each skip is a multiple of the wall thickness, the estimated crack depths should be equal to the transducer displacement along the inspection axis.

The above discussed methods are more fully described in the following U.S. patents and the reader is referred thereto for a more detailed discussion. In summary, U.S. Pat. No. 5,125,272 teaches the use of tip diffraction and longitudinal waves to determine the depth of a crack in a tube surface. U.S. Pat. No. 4,658,649 teaches an inspection system for surface cracks utilizing both shear waves and longitudinal waves. This reference also teaches the conversion of shear waves to longitudinal waves and the use of creeping longitudinal waves. U.S. Pat. No. 5,467,321 teaches the use of ultrasonic transducers with a mode conversion.

The discussed known methods have defects which do not allow for an accurate measurement of small cracks. In summary:

1. For thin wall tubing, crack gap is typically less than 1/10 wave length so the known tip method is rarely available for such sizing.
2. The multiple skip method provides only an estimate of the crack depth. The multiple skip indicates that the crack is "deep" or mathematically the crack depth is within one wave length of being through wall. No actual depth determination can be made using this method.
3. The target motion TOF method makes assumptions concerning the nature of the reflected signal that may be incorrect. Also, the earliest and latest detection may not coincide with the tip of the crack.

Thus an improved method of thin wall tube crack sizing was needed.

SUMMARY OF THE INVENTION

The present invention solves the problems associated with the discussed prior art sizing methods and other by providing a crack sizing method which uses a combination of depth crack sizing methods to improve crack sizing accuracy for thin walled tubing and tight (crack surface opening less than 0.001 inches) tube cracks of any depth. The tube wall can consist of a single material or multiple metallic electrode-posited materials with different magnetic properties such as Electrosleeve™.

The present method uses a combination of known depth sizing methods including the shear wave time of flight method and two new depth sizing methods. The two new methods are designated as the mode converted signal (MCS) method and the full skip normalization (FSN) method which when used in combination will measure thin wall tube cracks accurately as well as crack openings less than 0.001 in. for any thickness of tube even ones made up of differing material layers (electrodeposited or otherwise intimately bonded).

In view of the foregoing it will be seen that one aspect of the present invention is to provide an improved accuracy method for thin wall tubing sizing.

Another aspect is to provide an accurate method of measuring crack surface openings less than 0.001 in. for any thickness tube or plate.

Yet another aspect is to provide an improved accuracy crack sizing method for multiple material layered plates or tubes (electrodeposited or otherwise intimately bonded).

These and other aspects of the present invention will be more fully understood after a perusal of the following preferred description of the invention when considered in conjunction with the accompanying drawings.

BRIEF DESCRIPTION OF THE DRAWINGS

In the drawings:

FIG. 1 is a schematic description for a known tube crack sizing method using the "time of flight" (TOF) method;

FIG. 2 is a schematic description for a known tube crack sizing method using the "tip sizing method" (TSM);

FIG. 3 is a schematic description for a known tube crack sizing method using the "multiple skip method" (MSM);

FIG. 6 is a table comparing test results using conventional TOF analysis to MCS analysis;

FIG. 7 is a table listing test results using the full skip normalization techniques;

DESCRIPTION OF THE PREFERRED EMBODIMENT

The present invention proposes a refinement of a known depth sizing protocol (e.g. tip diffraction, multiple skip method and target motion time of flight—TOF) with two new depth sizing methods described below. The two new methods are designated as "mode converted signal" (MCS) and "full skip normalization" (FSN) methods.

These new tube crack depth sizing methods (MCS and FSN) can be successfully applied to size thin wall tube cracks or thick wall tube or plate cracks having small width cracks (below 1/10 wavelength) for any depth of the crack.

The present invention uses the MCS and FSN methods for depth sizing of cracks originating from the surface opposite to the incident surface of the sound wave.

The primary signal characteristics that are used to size planar defects are signal amplitude and time of flight. As the probe shear wave transducer moves closer to a detected indication, the flaw response signal reflections will occur earlier in time and will change in amplitude. The detected length of the target motion is used as a measure of indication depth. (Target motion is the apparent change in depth of an indication resulting from transducer motion.)

The present art target motion TOF sizing technique requires certain assumptions about the response signal target motion and TOF. Flaw examinations with subsequent destructive evaluations have indicated that these assumptions are partially incorrect for thin wall analysis.

With the assumption that crack responses are 45 degree shear wave returns, the transducer displacement from the location of the corner reflector to the crack tip reflection should correspond to the depth determined by the shear wave TOF. However, a significant discrepancy between the transducer displacement and the depth has been observed by the applicants. (As crack depth of penetration increases, the displacement versus depth discrepancy increases). One possible explanation for the displacement versus depth discrepancy is the existence of a mode-converted signal, as described below.

Basic Mode Conversion Theory

Figures 4, 5:
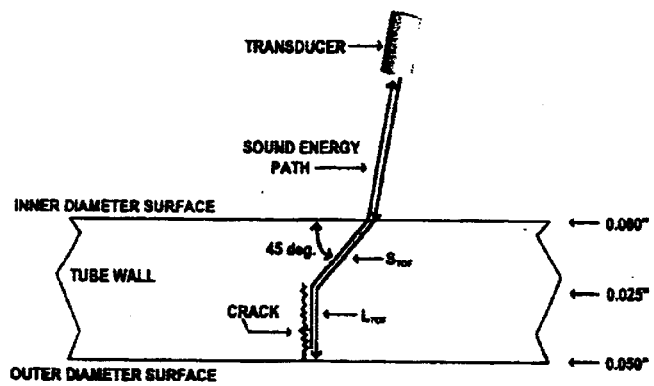
FIG. 4 is a schematic description of the "mode conversion method" (MCM) used in the present invention.
FIG. 5 is a table listing sizing test data using the mode converted signal sizing method.

A mode-converted signal is defined as the theorized conversion of the shear wave to a longitudinal wave at the point of incidence of the sound energy on the crack face. FIG. 4, with the associated definitions therein, describes the mode conversion method. While the mode conversion of the shear wave in general can be considered prior art, the conversion of the transverse wave to a longitudinal creeping wave at the point of incidence with the crack face and the subsequent correction of the errors in depth sizing associated with this phenomenon are unique. The correction coefficient for the depth sizing was determined from a mathematical model of the mode converted sound propagation and demonstrated experimentally.

In FIG. 4, the symbols are defined as follows:

$S_{TOF}$=time of flight associated with a shear wave traveling at a 45° angle in the tube wall to a depth of 0.025 inches or (0.025 in.)*(1/sin 45°), path distance at a shear wave velocity of 0.1217 in./μs.

$L_{TOF}$=time of flight associated with a longitudinal wave traveling at a 0° normal angle along the crack face to the outer diameter interface for a distance of 0.025 inches at a longitudinal velocity of 0.233 in./μs.

Experimental Verification

In an experimental setup, a second transducer, placed on the outside of the tube, was used to confirm the presence of the longitudinal wave. The second transducer detected repeating waveforms with time of flight separations equal to the time required to traverse the wall thickness at the longitudinal velocity of sound for the Inconel-600 material. From the mathematical model and the experimental results, it can be stated that the shear wave is converted to a longitudinal wave at the point of incidence with a planar reflector that is perpendicular to the originating surface.

Any sizing technique which interprets depth as a function of shear wave time of flight will have an error proportional to the additional time of flight associated with the longitudinal wave's propagation to a reflecting interface, (inner or outer diameter surface).

Based on research, for a 45 degree shear wave conversion to a longitudinal wave, a correction factor of 1.6 is required to correct the measured depth of penetration. The error correction factor is the ratio of actual depth to the uncorrected TOF depth prediction from the mathematical model. Table 1 found in FIG. 5 shows the uncorrected depth measurement associated with the existing target motion time of flight analysis, uncorrected TOF depth prediction from the mathematical model, mode conversion TOF corrected depth prediction, and the depth measurement error of the mode conversion call for a series of outer diameter initiated EDM notches. The uncorrected TOF depth predictions were determined using the Depth of Penetration results from the mathematical model of the sound propagation shown in FIG. 4 for each notch depth. The mode conversion TOF corrected depth predictions were determined by multiplying the uncorrected depth measurement from the target motion TOF analysis by 1.6.

From Table 1 data we can see the following:

The UNCORRECTED UT DEPTH ESTIMATE is the UT system depth measurement based on the shear wave target motion time of flight (TM TOF) analysis.

The UNCORRECTED TOF DEPTH PREDICTION is a theoretical calculation of the mode converted TOF and the depth prediction which would result from the mode converted TOF (the model).

The TM TOF DEPTH ERROR is the difference between the actual NOTCH DEPTH and the UNCORRECTED UT DEPTH ESTIMATE.

The CORRECTED TOF DEPTH PREDICTION is the UNCORRECTED UT DEPTH ESTIMATE value multiplied by the 1.6 correction factor, from the model, to account for the mode converted signal TOF.

MCS CORRECTED DEPTH ERROR is the difference between the actual NOTCH DEPTH and the CORRECTED TOF DEPTH PREDICTION.

Note that there is clear agreement between the measured UNCORRECTED UT DEPTH ESTIMATE and the theoretical UNCORRECTED TOF DEPTH PREDICITON (verification of the model).

The use of the 1.6 correction multiplier, to account for mode conversion, produces better depth size estimates. The correction factor for a specific probe would be derived from the analysis of the target motion time of flights from a calibration standard's EDM notches and has values between 1.6 and 1.9.

The upper bound for the correction factor is the ratio of the longitudinal and shear sound velocity (0.233/0.1217). Velocities are expressed in inches per microsecond. Variations in the correction multiplier are a result of the actual propagation angle of the sound in the material. The model assumed 45° since this was the design value.

The advantages of the use of the MCS method are best shown by referring to Table 2 found in FIG. 6 which shows a comparison of the MCS technique to the conventional TOF analysis. The parameters used for the comparison are the average sizing error, error standard deviation, the maximum under-call, the RMSE and the Lower 95% confidence limit. Assuming a normal error distribution, the lower 95% confidence level is calculated by subtracting 1.645 times the error standard deviation from the average sizing error. Although the data is based on EDM notches, Table 2 is significant in the relative comparison between the conventional target motion TOF analysis and the MCS corrected analysis on the same EDM flaws.

It is clear that the MCS technique provides a substantial improvement over target motion TOF analysis in sizing performance.

The Full Skip Normalization (FSN) sizing method compares the full skip return amplitude to the average of the outer diameter skip return amplitudes to yield improved depth of penetration determinations. This method provides a refinement of the depth determination when multiple sip information is available. By comparing the full skip return to the average of the outer diameter skip returns, the effect of electronic system gain is eliminated. This normalized result can be used to quantify the flaw depth of penetration.

Basic Full Skip Normalization Theory

According to the invention the ratio of the full skip amplitude to the average of the outer diameter skip amplitudes produces a normalized result. The ratio was developed as part of the investigation to support the use of the full skip information to estimate the depth of a defect that propagates from the outer diameter surface. For example, a transducer with a frequency of 10 MHz normalized values in excess of 0.50 results in the determination that less than 0.015 inches of material thickness remains between the ends of the OD initiated crack and the inner diameter surface (Table 3 found in FIG. 7).

The FSN method is based on the fact that as the crack depth of penetration increases, the remaining wall material decreases and the full skip signal response amplitude increases. This is significant in that as the crack depth increases, the signal used to characterize the depth improves. Simply stated, as a crack proceeds to the inner diameter surface, a full skip corner reflection signal will develop. The characteristic can be used to provide an improved estimate of the depth of penetration of a crack propagating from a tube's outer diameter.

Normalized Result is, according to the invention, the ratio of the 1 skip amplitude to the average of the two outer diameter skips, (½ skip and the 1 & ½ skip). This ratio can be used to depth size deep cracks propagating from the surface opposite of the UT transducer.

Experimental Verification

Table 3 (found in FIG. 7) provides typical FSN values for various depths of penetration of outer diameter EDM notches in a 0.050" thick wall.

The remaining wall @ EDM is the difference between the EDM depth of penetration and the wall thickness 0.050". For example, a 0.040" deep notch has a remaining wall of 0.050"−0.040"=0.010"

N/A denotes no full skip waveform detection.

Testing has demonstrated that the FSN sizing method is independent of system gain, probe acquisition pitch and signal saturation. Signal saturation is defined as signal amplitude in excess of the input voltage range of the analog to digital converter (the signal processor).

The combined results from the testing were used to develop a regression equation for converting the FSN value to a remaining wall (REMAINING WALL @EDM) measurement. The FSN values for twelve (12) test cases were averaged. Plotting these averaged FSN ratios versus the remaining wall thickness revealed a linear relationship for remaining walls less than 0.025 inch. A linear regression analysis was performed using the averaged FSN test case results for each notch to develop a formula to convert the FSN ratio to remaing wall. For a 10 MHz transducer, the regression produced a correlation coefficient value of 0.998 for the following formula:

$$\text{REMAINING WALL}=0.031 \text{ inches}-\text{FSN}*0.031$$

Advantages of Using the FSN Technique

Figures 8, 9:
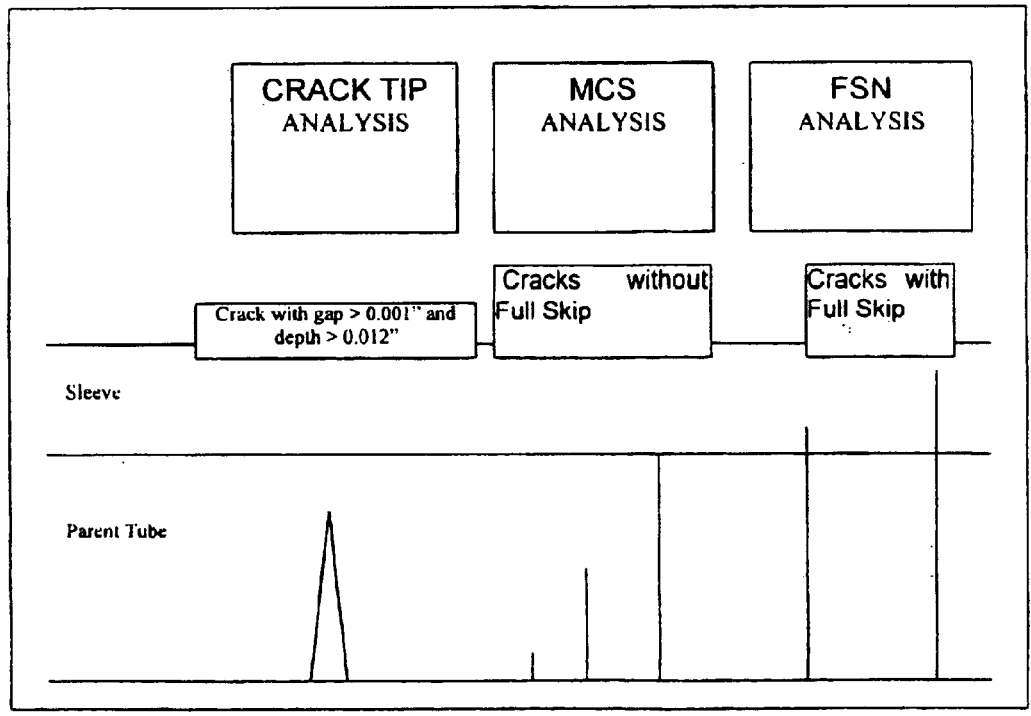
FIG. 8 is a table listing the comparison between FSN measurements and actual remaining wall thickness of a tube.
FIG. 9 is a logic schematic of the combined test methods of the present invention.

An error analysis was performed using the above regression for outer diameter stress corrosion cracks (ODSCC)

with actual remaining wall determinations and recorded in Table 4 found in FIG. 8. For each crack, the FSN value and the regression estimate were calculated for four circumferential locations that have corresponding destructive examination (DE) results.

The delta value of 0.007 represents an over-call for the crack depth, while the delta value of −0.003 represents an under-call for the crack depth. The use of the regression improves the depth sizing for both samples, as compared to the conventional TM TOF method or a multiple skip "deep" determination.

Using a Combination of Sizing Methods to Produce Improved Sizing Measurements

According to the invention the combination of crack sizing methods is applied as follows:

If there is a tip signal in the shear wave response, it will be used to determine the crack depth.

If there is a half skip signal response but no full skip information, the mode converted signal correction (MCS) will be applied to the shear wave TOF sizing analysis.

If there are OD skip responses in addition to a full skip signal response, the FSN analysis will be applied.

The strength of the FSN analysis technique is that the sizing accuracy increases as the remaining wall thickness decreases below a wave length for a given transducer frequency.

FIG. 9 shows the UT crack sizing technique logic of the present invention as applied to the case of an electrodeposition or otherwise intimately bonded layers of materials with different magnetic properties inside a thin tube or plate. This order of analysis is in agreement with the strengths of each analysis technique. The tip diffraction analysis has been shown to be the most accurate if the tip signal can be detected and verified. Tip signals are typically present with cracks having significant volume and considerable depth. For example in the case of tight cracks that are partial through wall from the tube OD, the mode converted signal correction provides the most accurate measure of crack depth. Finally, as a tight OD crack propagates closer to the inner diameter surface, and into the electro-deposition, the probability of detecting a full skip signal reflection increases. For nominal 10 MHz transducers, testing has shown the full skip signal has a very strong response with a remaining wall of 0.015 inches, but may be detected at remaining wall values up to 0.025 inches (Table 3).

One application of the above described tube crack sizing method of the present invention is for a basic ODSCC analysis as follows (in time line form). The same logic applies for examining thin plates.

1. Review data for signal reflections at I/2 skip, full skip and 1 I/2 skip locations.
2. If reflections present, look for crack tip signal.
3. If crack tip signal can be verified, use crack tip signal to size crack.
4. If no crack tip signal can be verified, but reflections are present at the I/2 and II/2 skip locations, then use target motion TOF with MCS correction.
5. If full skip signal is present in addition to the I/2 skip and I I/2 skip signals, then use the FSN sizing technique.

It will be understood that certain obvious modifications and improvements have been deleted herein for the sake of conciseness and readability but are properly within the scope of the following claims.

We claim:

1. A method of sizing surface cracks in a metal surface using sound wave measurements of propagation and reflection thereof which are initiated at an optimal degree angle to the surface comprising the steps of:

acquire sound wave data by displacing a transducer along the direction of propagation of the sound waves;

review the acquired signals for a crack tip signal;

review the acquired sound wave data for signal reflections at ½ skip, full skip and 1½ skip locations, when ½ skip, full skip and 1½ skip reflections are detected reviewing reflected signal data to determine if no crack tip signal was detected and that reflections are present at the ½ and 1½ skip locations;

using target motion time of flight (TOF) data to estimate the depth of the crack and correcting the TOF depth estimate for a mode converted signal (MCS) with MCS correction to size the surface crack only if no full skip reflection signal is present.

2. A method as set forth in claim 1 including the further steps of:

reviewing signal reflected data to determine if full skip signal was present in addition to the ½ skip and 1½ skip signals;

using the ratio of the 1 skip amplitude to the average of the ½ skip and 1½ skip amplitudes to size the surface crack whenever all three of the above signals are present.

3. A method as set forth in claim 2, wherein the sound waves are waves measured by an ultrasonic transducer initiated at an appropriate angle to the metal surface being tested.

4. A method as set forth in claim 3 wherein the metal surface is a composite or otherwise intimately bonded layer of metal tube or plate having a crack width less than 0.001 in.

5. A method of sizing surface cracks in a metal surface as set forth in claim 1, wherein the TOF depth estimate is the UT system depth measurement based on a conventional shear wave target motion time of flight (TOF) analysis.

6. A method as set forth in claim 5, wherein the MCS correction comprises multiplying the TOF depth estimate by a MCS correction factor.

7. A method as set forth in claim 6 wherein the metal surface is a thin wall tube and the MCS correction factor is determined experimentally and is between 1.6 and 1.9.

8. A Full Skip Normalization FSN method using the ratio of a full skip signal amplitude to the average of outer diameter skip signal amplitudes to depth size deep cracks propagating from a surface located opposite from a UT transducer comprising the steps of:

measuring a full skip signal amplitude;

measuring a series of outer diameter signal amplitudes;

averaging said series of outer diameter signal amplitudes;

forming a ratio of the measured full skip signal amplitude to the averaged series of outer diameter amplitudes; and converting the ratio of the full skip signal amplitude to averaged outer diameter amplitudes to a remaining wall thickness using an empirically derived formula.

9. A method as set forth in claim 8 where for the given application of the thin wall tubing with thickness approximately 0.050 inches, the remaining wall thickness is obtained by the following formula:

Remaining Wall (inches)=0.031−FSN ratio*0.031.

* * * * *